US012616670B2

(12) United States Patent
Hartmann et al.

(10) Patent No.: US 12,616,670 B2
(45) Date of Patent: May 5, 2026

(54) N-PHENYL-3-MERCAPTOPROPANAMIDE DERIVATIVES AS METALLO-BETA-LACTAMASE INHIBITORS FOR THE TREATMENT OF BACTERIAL INFECTIONS

(71) Applicant: Helmholtz-Zentrum Fur Infektionsforschung GmbH, Braunschweig (DE)

(72) Inventors: Rolf W. Hartmann, Braunschweig (DE); Jelena Konstantinovic, Braunschweig (DE); Jörg Haupenthal, Braunschweig (DE); Anna K. Hirsch, Braunschweig (DE); Andreas M. Kany, Braunschweig (DE); Cansu Kaya, Braunschweig (DE); Samir Yahiaoui, Braunschweig (DE); Thomas Wichelhaus, Frankfurt (DE); Eugen Proschak, Frankfurt (DE)

(73) Assignee: HELMHOLTZ-ZENTRUM FÜR INFEKTIONSFORSCHUNG GmbH, Braunschweig (DE)

( * ) Notice: Subject to any disclaimer, the term of this patent is extended or adjusted under 35 U.S.C. 154(b) by 684 days.

(21) Appl. No.: 17/913,490

(22) PCT Filed: Mar. 23, 2021

(86) PCT No.: PCT/EP2021/057461

§ 371 (c)(1),
(2) Date: Sep. 22, 2022

(87) PCT Pub. No.: WO2021/191219

PCT Pub. Date: Sep. 30, 2021

(65) Prior Publication Data

US 2023/0146507 A1 May 11, 2023

(30) Foreign Application Priority Data

Mar. 23, 2020 (EP) .................................... 20164855

(51) Int. Cl.

| | |
|---|---|
| ***A61K 31/196*** | (2006.01) |
| ***A61K 31/167*** | (2006.01) |
| ***A61K 31/18*** | (2006.01) |
| ***A61K 31/245*** | (2006.01) |
| ***A61K 31/407*** | (2006.01) |
| ***A61K 31/495*** | (2006.01) |
| ***A61K 31/5375*** | (2006.01) |
| ***A61K 31/64*** | (2006.01) |
| ***A61P 31/04*** | (2006.01) |
| ***C07C 311/08*** | (2006.01) |
| ***C07C 311/46*** | (2006.01) |
| ***C07C 311/58*** | (2006.01) |
| ***C07C 311/64*** | (2006.01) |
| ***C07C 323/41*** | (2006.01) |
| ***C07D 295/135*** | (2006.01) |
| ***C07D 295/26*** | (2006.01) |

(52) U.S. Cl.

CPC .......... *A61K 31/196* (2013.01); *A61K 31/167* (2013.01); *A61K 31/18* (2013.01); *A61K 31/245* (2013.01); *A61K 31/407* (2013.01); *A61K 31/495* (2013.01); *A61K 31/5375* (2013.01); *A61K 31/64* (2013.01); *A61P 31/04* (2018.01); *C07C 311/08* (2013.01); *C07C 311/46* (2013.01); *C07C 311/58* (2013.01); *C07C 311/64* (2013.01); *C07C 323/41* (2013.01); *C07D 295/135* (2013.01); *C07D 295/26* (2013.01)

(58) Field of Classification Search

CPC .................................................... A61K 31/196

See application file for complete search history.

(56) References Cited

U.S. PATENT DOCUMENTS

2012/0302815 A1* 11/2012 Chen .................. C07K 5/06043 435/375
2015/0065534 A1* 3/2015 Goodnow, Jr. ........ C07H 21/02 548/546

(Continued)

FOREIGN PATENT DOCUMENTS

CN 108 117 502 A 6/2018
CN 108690119 A * 10/2018 ........... A61K 31/537

(Continued)

OTHER PUBLICATIONS

Wang et al., Molybdenum-Mediated Desulfurization of Thiols and Disulfides, Synlett, 2014, 25, 1869-1872.*

(Continued)

*Primary Examiner* — Svetlana M Ivanova
(74) *Attorney, Agent, or Firm* — Fox Rothschild LLP; Peter F. Corless

(57) ABSTRACT

The present invention related to novel inhibitors of metallo-β-lactamases of formula (I)

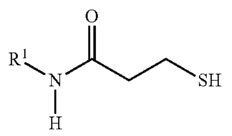

wherein $R^1$ is an optionally substituted aryl group of an optionally substituted heteroaryl group, and the use thereof in the treatment of bacterial infections, especially in combination with β-lactam antibiotics.

20 Claims, No Drawings

(56) References Cited

U.S. PATENT DOCUMENTS

| | | | | |
|---|---|---|---|---|
| 2016/0159766 | A9* | 6/2016 | Buysse | A01N 43/653 544/131 |
| 2017/0049899 | A1* | 2/2017 | Chimmanamada | A61K 31/4745 |
| 2018/0189250 | A1* | 7/2018 | Lee | G06F 40/166 |
| 2019/0202839 | A1* | 7/2019 | Jain | A61K 47/68033 |

FOREIGN PATENT DOCUMENTS

| | | | | |
|---|---|---|---|---|
| EP | 0 157 241 | A1 | 10/1985 | |
| WO | 96/07658 | A1 | 3/1996 | |
| WO | WO-2007102069 | A1 * | 9/2007 | A61K 31/404 |
| WO | WO-2013119954 | A1 * | 8/2013 | A61K 31/439 |

OTHER PUBLICATIONS

Clavaud et al., Combinatorial self-assembly of cyclophilin hCyp-18 ligands through rhenium coordination, Chembiochem. Sep. 2006; 7(9):1352-5.*
Forster et al., 2-Sulfonylpyrimidines Target the Kinesin HSET via Cysteine Alkylation, European Journal of Organic Chemistry, 2-Sulfonylpyrimidines Target the Kinesin HSET via Cysteine Alkylation, vol. 2019, Issue 31-32, Special Issue: Heterocyclic Chemistry, Sep. 1, 2019, pp. 5486-5496.*
Trist et al., 4,6-Diphenylpyridines as Promising Novel Anti-Influenza Agents Targeting the PA-PB1 Protein-Protein Interaction: Structure-Activity Relationships Exploration with the Aid of Molecular Modeling, J Med Chem. Mar. 24, 2016;59(6):2688-703.*
STN document No. 171:197230, Oct. 24, 2018.*
STN document No. 169:113304, Jun. 22, 2018.*
STN document No. 168:366877, Mar. 22, 2018.*
STN document No. 164:349912, Mar. 3, 2016.*
STN document No. 163:427377, Sep. 11, 2015.*
STN document No. 159:348356, Aug. 2, 2013.*
STN document No. 158:3897, Nov. 29, 2012.*
STN document No. 157:605752, Oct. 11, 2012.*
STN document No. 156:158700, Dec. 9, 2011.*
STN document No. 151:456149, Oct. 15, 2009.*
STN document No. 148:189401, Feb. 1, 2008.*
STN document No. 147:357141, Sep. 12, 2007.*
STN document No. 145:397187, Aug. 10, 2006.*
STN document No. 144:430805, Mar. 16, 2006.*
STN document No. 139:341741, Oct. 24, 2003.*
STN document No. 136:66199, Dec. 21, 2001.*
STN document No. 136:167326, Dec. 9, 2001.*
STN document No. 136:2190, Sep. 20, 2001.*
STN document No. 134:147369, Nov. 29, 2000.*
STN document No. 133:222918, Jun. 26, 2000.*
STN document No. 126:171890, Jan. 23, 1997.*
STN document No. 123:306084, Sep. 23, 1995.*
STN document No. 117:223002, Nov. 28, 1992.*
STN document No. 116:224641, May 31, 1992.*
STN document No. 115:102789, Sep. 6, 1991.*
STN document No. 101:230000, Dec. 22, 1984.*
STN document No. 50:28238, Apr. 22, 2001.*
F.M. Klingler et al., "Approved Drugs containing Thiols as Inhibitors of Metallo-#-Lactamasdes: a Strategy to Combat Multidrug-Resistant Bacteria", Journal of Medicinal Chemistry, pp. 1-7, Apr. 3, 2015.
K. Bush et al., "Interplay between b-lactamases and new b-lactamase inhibitors", Nature Reviews, vol. 17, pp. 295-306, May 2019.
S.E. Ho et al., "Carbapenem-Resistant Pseudomonas aeruginosa in Malaysia Producing IMP-7 b-Lactamase", Antimicrobial Agents and Chemotherapy, 46(10), pp. 3286-3287 (Oct. 2002).
N. Franceschini et al., "Purification and Biochemical Characterization of the VIM-1 Metallo-b-Lactamase", Antimicrobial Agents and Chemotherapy, 44(11), pp. 3003-3007 (Nov. 2000).
M. McKenna, "The Last Resort: Health officials are watching in horror as bacteria become resistant to powerful carbapenem antiobiotics—one of the last drugs on the shelf", Nature, vol. 499, pp. 394-396 (Jul. 25, 2013).
Y. Guo et al., "A structural view of the antibiotic degradation enzyme NDM-1 from a superbug", Protein Cell, 2(5), pp. 384-394 (2011).
C. Chakraborty et al., "Zebrafish: A complete animal model to enumerate the nanoparticle toxicity", Journal of Nanobiotechnology, 14(65), pp. 1-13 (2016).
C.A. MacRae et al., "Zebrafish as tools for drug discovery", Nature Reviews-Drug Discovery, vol. 14, pp. 721-731 (Oct. 2015).
M.F. Mojica et al., "B1-Metallo-besta-Lactamases: Where do we stand?", Current Drug Tarts, pp. 1-44 (Jan. 1, 2017).
M.P. Weinstein, MD et al., "Methods for Dilution Antimicrobial Susceptibility Tests for Bacteria That Grow Aerobically", Clinical and Laboratory Standards Institute, 11th Edition, Jan. 2018.
J. Haupenthal et al., "RNAse A-like enzymes in serum inhibit the anti-neoplastic activity of siRNA targeting Polo-like kinase 1", Int. J. Cancer, Volumn 121, pp. 206-210 (2007).
C.D.Doen, "When Does 2 Plus 2 Equal 5? A Review of Antimicrobial Synergy Testing", Journal of Clinical Microbiology, 52(12), pp. 4124-4128 (Dec. 2014).
J. Maes et al., "Evaluation of 14 Organic Solvents and Carriers for Screening Application sin Zebrafish Embryos and Larvae", PLoS One 7(10): e43850. https://dol.org/10.1371/journal.pone.0043850, pp. 1-10.
International Search Report issued Dec. 5, 2021 in PCT Application No. PCT/EP2021/057461.
C. Clavaud et al., "Combinatorial Self-Assembly of Cyclophilin hCyp-18 Ligands through Rhenium Coordination", Chembiochem, 7(9), pp. 1352-1355 (Sep. 4, 2006).
T. Förster et al., "2-Sulfonylpyrimidines Target the Kinesin HSET via Cysteine Alkylation", European Fournal of Organic Chemistry, 2019(31-32), pp. 5486-5496 (Jun. 4, 2019).
Z. Wang et al., "Molybdenum-Mediated Desulfurization of Thiols and Disulfides", Synlett, 25(13), pp. 1869-1872, Jun. 6, 2014.
I.M.L. Trist et al., "4,6-Diphenylpyridines as Promising Novel Anti-Influenza Agents Targeting the PA-PB1 Protein-Protein Interaction: Structure-Activity Relationships Exploration with the Aid of Molecular Modeling", Journal of Medicinal Chemistry, 59(6), pp. 2688-2703, Mar. 11, 2016.

* cited by examiner

N-PHENYL-3-MERCAPTOPROPANAMIDE DERIVATIVES AS METALLO-BETA-LACTAMASE INHIBITORS FOR THE TREATMENT OF BACTERIAL INFECTIONS

This application is a National Stage Application pursuant to 35 U.S.C. § 371, of United States International Application No. PCT/EP2021/057461, filed Mar. 23, 2021, which claims priority to European Patent Application No. 20164855.7, filed Mar. 23, 2020. The entire contents of which are incorporated herein by reference in their entirety.

The present invention relates to novel N-aryl mercaptopropionamides and the use thereof as inhibitors of metallo-β-lactamases. In combination with β-lactam antibiotics, these compounds are useful in the treatment of infections, especially due to antibiotic-resistant bacteria.

Antibiotic resistance is a severely intensifying threat to human health, as it leads to diseases that are extremely difficult to cure. Over the years, many bacteria have established various ways of resistance including the secretion of beta-lactamases, which are enzymes able to hydrolyze the β-lactam ring of highly effective antibiotics such as penicillins, cephalosporins, carbapenems and monobactams (Proschak, E. et al, (2015) *J. Med. Chem.* 58, 3626-3630). The affected bacteria include important pathogens such as *Pseudomonas aeruginosa* and Enterobacterales (e.g. *Escherichia coli*). Since their first discovery, β-lactam antibiotics are still the most used antibacterial drugs, especially for infections caused by these bacteria. However, their efficacy is threatened by above-mentioned beta-lactamases.

The two most significant categories of beta-lactamases are based on their catalytic mechanism. Class A, C and D contain serine beta-lactamases (SBLs) which cleave the β-lactam ring by a nucleophilic attack of the serine residue, whereas class B contains metallo-beta-lactamases (MBLs) bearing one or two zinc cations in the active site and hydrolyze the active center of β-lactam antibiotics by a nucleophilic water molecule (Bush, K., Bradford, P. A. (2019). Nat. Rev. Microbiol. 17, 459-460).

Beta-lactamases belonging to class B are further divided into B1, B2 and B3 based on their sequence identity. B1 MBLs contain the largest number of clinically relevant members, including VIMs (Verona integrin-encoded MBLs), IMPs (Imipenemase) and NDMs (New Delhi MBLs) (Mojica, M. F., Bonomo, R. A., & Fast, W. (2016). *Current drug targets,* 17, 1029-1050). There are many variants of each of these members, since the selective pressure continues to initiate the evolution of resistance. Some of the common features they share are low sequence identity, exhibition of a similar protein fold, and having a broad substrate profile.

IMP enzymes are the first isolated member of MBLs. Up to today, more than 47 variants of IMP-1 have been identified, which are mostly encoded by *P. aeruginosa*. IMP-7 showed high resistance to late-generation carbapenems meropenem and imipenem (Navaratnam, P. et al, (2002). *Antimicrobial agents and chemotherapy,* 46, 3286-3287).

VIM-type MBLs constitute the second major subgroup after IMPs, which has first been isolated from *P. aeruginosa*. The initial biochemical characterization of VIM-1 showed that it exhibits a broad substrate specificity including all β-lactam antibiotics except monobactams (Docquier J-D. et al, (2000). *Antimicrob Agents Chemother,* 44, 3003-3007).

NDM type MBLs form the third main type with more than 15 variants. It has spread to nearly every continent worldwide and has become a tremendous threat to the world (McKenna M. (2013). Nature, 499, 394-396). Although it has been known for a shorter time than the other two, the crystal structure of NDM-1 was reported in 2011 (Rao, Z. et. al, (2011). Prot Cell. 2, 384-94). The structure displays two catalytic zinc ions bound as dinuclear center in the active site and it provided considerable insight into ligand recognition by NDM-1.

Given that the pipeline of new antibiotics is virtually empty, an alternative way to treat infections caused by multi-drug resistant pathogens is through design of novel beta-lactamase inhibitors. These inhibitors usually have no intrinsic antibacterial activity but restore the activity of currently used β-lactam antibiotics by inhibiting beta-lactamases.

There are numerous SBL inhibitors in clinical use, whereas class B1 MBL inhibitors remain challenging to progress further. The fact that MBLs can hydrolyze almost all β-lactam antibiotics, including carbapenem, is the main drawback for the development of new structures. Moreover, it is difficult to make a generalization based on the active site, as there is a high sequence variation within this subfamily and the β-lactam substrates are quite diverse. Even though many potent inhibitors were reported in literature, their effect is usually restricted to only one of the MBL types within the sub-class. However, it is advantageous to have broad-spectrum inhibitors that are active against most of the relevant members belonging to this class.

The beta-lactamases found in Gram-positive organisms are often extracellular enzymes. However, in Gram-negative organisms, beta-lactamases are almost always restricted to the periplasmic space. This constitutes a problem, because the outer membrane of Gram-negative bacteria in general restricts the transport of a multitude of molecules. Consequently, permeability properties and the risk for efflux should be considered during the design and development of new MBL inhibitors.

Both zinc-independent and zinc-dependent approaches to the design of new inhibitors have their disadvantages. For Zn-independent inhibitors, the lack of common amino acids and the absence of a deep active site pocket is a problem. The challenge for Zn-dependent inhibitors is their selectivity towards many other metalloenzymes involved in the metabolism, such as matrix metalloproteinases (MMPs). Selectivity against such off-targets is very desirable in the development of new compounds, so that the inhibitors can progress in the clinic.

All the aforementioned reasons create a lack of effective inhibitors to overcome MBL-mediated resistance and make class B MBLs attractive targets to focus on.

The compounds of the present invention provide a high activity against three important B1 MBLs. In addition, they show no antibacterial activity, whereas when combined with imipenem, they restore its activity, reducing MIC values up to 60-fold. The potency of these compounds is supported by high selectivity over different off-targets. The compounds of the present invention are especially advantageous in terms of broad-spectrum MBL activity.

The present invention provides compounds of formula (I)

(I)

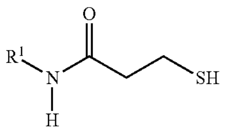

wherein $R^1$ is an optionally substituted aryl group or an optionally substituted heteroaryl group, or a pharmaceutically acceptable salt thereof.

Preferably, $R^1$ is an optionally substituted phenyl group, an optionally substituted naphthyl group or an optionally substituted heteroaryl group containing from 5 to 10 ring atoms (e.g. 5, 6, 9 or 10 ring atoms) selected from C, O, N and S.

Especially preferably, $R^1$ is an optionally substituted phenyl group or an optionally substituted heteroaryl group containing 5 or 6 ring atoms selected from C, O, N and S.

Most preferably, $R^1$ is an optionally substituted phenyl group.

The term "optionally substituted" refers to a group which is unsubstituted or substituted by one or more (especially by one, two or three; preferably by one or two; especially preferably by one) substituents.

If group $R^1$ comprises more than one substituent, these substituents are independently selected, i.e., they may be the same or different.

Examples for substituents are fluorine, chlorine, bromine and iodine and OH, SH, $NH_2$, $—SO_3H$, $—SO_2NH_2$, —COOH, —COOMe, —COMe, $—NHSO_2Me$, $—SO_2NMe_2$, $—CH_2NH_2$, NHAc, $—SO_2Me$, $—SO_2NCNH_2NH_2$, $—CH_2N(CH_2CH_3)_2$, $—SO_2NHCONH_2$, $—SO_2NHC(NH)NH_2$,

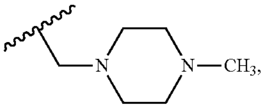

$(—CH_2N(CH_2CH_2)_2NCH_3)$

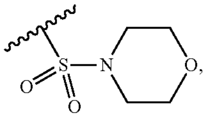

$(—SO_2—N(CH_2CH_2)_2O)$ $—CONH_2$, —CN, $—NHCONH_2$, $N_3$ and $NO_2$ groups. Further examples of substituents are $C_1$-$C_{10}$ alkyl, $C_2$-$C_{10}$ alkenyl, $C_2$-$C_{10}$ alkynyl, $C_1$-$C_{10}$ heteroalkyl, $C_3$-$C_{18}$ cycloalkyl, $C_2$-$C_{17}$ heterocycloalkyl, $C_4$-$C_{20}$ alkylcycloalkyl, $C_2$-$C_{19}$ heteroalkylcycloalkyl, $C_6$-$C_{18}$ aryl, $C_1$-$C_{17}$ heteroaryl, $C_7$-$C_{20}$ aralkyl and $C_2$-$C_{19}$ heteroaralkyl groups; especially $C_1$-$C_6$ alkyl, $C_2$-$C_6$ alkenyl, $C_2$-$C_6$ alkynyl, $C_1$-$C_6$ heteroalkyl, $C_3$-$C_{10}$ cycloalkyl, $C_2$-$C_9$ heterocycloalkyl, $C_7$-$C_{12}$ alkylcycloalkyl, $C_2$-$C_{11}$ heteroalkylcycloalkyl, $C_6$-$C_{10}$ aryl, $C_1$-$C_9$ heteroaryl, $C_7$-$C_{12}$ aralkyl and $C_2$-$C_{11}$ heteroaralkyl groups, further preferably $C_1$-$C_6$ alkyl and $C_1$-$C_6$ heteroalkyl groups.

Preferred substituents are halogen atoms (e.g. F, Cl, Br) and groups of formula —OH, $—O—C_{1-6}$ alkyl (e.g. —OMe, —OEt, —O-nPr, —O-iPr, —O-nBu, —C-iBu and —O-tBu), $—NH_2$, $—NHC_{1-6}$ alkyl, $—N(C_{1-6}$ alkyl$)_2$, —COOH, —COOMe, —COMe, $—NHSO_2Me$, $—SO_2NMe_2$, $—SO_3H$, $—SO_2NH_2$, $—CONH_2$, $—CH_2NH_2$, $—CH_2N(CH_2CH_3)_2$, $—SO_2NHCONH_2$, $—SO_2NHC(NH)NH_2$, $—CH_2N(CH_2CH_2)_2NCH_3$, —CN, $—C_{1-6}$ alkyl (e.g. -Me, -Et, -nPr, -iPr, -nBu, -iBu, -tBu and $—CF_3$), —SH, $—S—C_{1-6}$ alkyl, NHAc, $—SO_2—N(CH_2CH_2)_2O$, $—SO_2NCNH_2NH_2$, $—NO_2$, —C≡CH, $—NHCONH_2$, $—SO_2Me$ and cyclopropyl.

A further preferred substituent is a heteroalkyl group containing from 1 to 6 carbon atoms and from 1 to 6 heteroatoms that are independently selected from O, S and N.

A moreover preferred substituent is a group of formula $—X—R^{1a}$, wherein X is O, S, SO, $SO_2$, NH, $NHSO_2$, $CH_2$ or CO and $R^{1a}$ is an optionally substituted $C_{3-8}$ cycloalkyl group or an optionally substituted heterocycloalkyl group containing from 3 to 8 ring atoms that are independently selected from C, O, S and N. Preferably, X is $SO_2$ or $CH_2$. Further preferably, $R^{1a}$ is unsubstituted or substituted by a methyl group.

A further preferred substituent is a group of formula $—Y—R^{1b}$, wherein Y is $SO_2$, $SO_2NH$ or $NHSO_2$ and $R^{1b}$ is a hydroxy group, a $C_{1-6}$ alkyl group or a $C_{1-6}$ heteroalkyl group.

A moreover preferred substituent is F, Cl, OH, COOH, $NO_2$ or $NH_2$.

The substituent(s) is/are especially preferably independently selected from halogen (especially F and Cl) and —OH, $—NH_2$, —COOH, —COOMe, —COMe, $—NHSO_2Me$, $—SO_2NMe_2$, $—CH_2NH_2$, $—NO_2$, $—SO_2—N(CH_2CH_2)_2O$, $—SO_3H$, $—CH_2N(CH_2CH_3)_2$, $—SO_2NHCONH_2$, $—SO_2NHC(NH)NH_2$, $—CH_2N(CH_2CH_2)_2NCH_3$ and $—SO_2NCNH_2NH_2$.

The most preferred compounds of the present invention are the compounds disclosed in the examples, or a salt thereof.

Especially preferred are the following compounds, or a salt thereof:

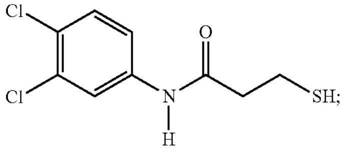

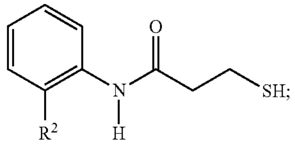

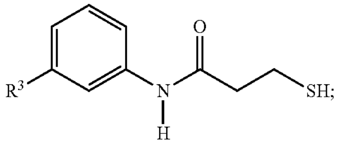

and

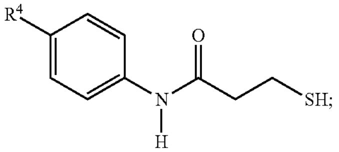

wherein $R^2$ is —COOH, $—NHSO_2Me$, —OH or —COOMe; $R^3$ is —OH, —COOH, $—NHSO_2Me$, $—CH_2NH_2$, $—NO_2$, $—SO_3H$ or $—CH_2N(CH_2CH_3)_2$; and $R^4$ is —OH, $—NH_2$, —COOH, —COOMe, —COMe, $—NHSO_2Me$, $—SO_2NMe_2$, $—SO_2—N(CH_2CH_2)_2O$, $—SO_2NHCONH_2$, $—SO_2NHC(NH)NH_2$ or $—CH_2N(CH_2CH_2)_2NCH_3$.

The expression alkyl refers to a saturated, straight-chain or branched hydrocarbon group that contains from 1 to 20 carbon atoms, preferably from 1 to 15 carbon atoms, especially from 1 to 10 (e.g. 1, 2, 3 or 4) carbon atoms, for example a methyl (Me, $CH_3$), ethyl, propyl, iso-propyl, n-butyl, iso-butyl, sec-butyl, tert-butyl, n-pentyl, iso-pentyl, n-hexyl, 2,2-dimethylbutyl or n-octyl group.

The expression $C_{1-6}$ alkyl refers to a saturated, straight-chain or branched hydrocarbon group that contains from 1 to 6 carbon atoms. The expression $C_{1-4}$ alkyl refers to a saturated, straight-chain or branched hydrocarbon group that contains from 1 to 4 carbon atoms. Examples are a methyl (Me), $CF_3$, ethyl, propyl, iso-propyl, n-butyl, iso-butyl, sec-butyl or tert-butyl group.

The expressions alkenyl and alkynyl refer to at least partially unsaturated, straight-chain or branched hydrocarbon groups that contain from 2 to 20 carbon atoms, preferably from 2 to 15 carbon atoms, especially from 2 to 10 (e.g. 2, 3 or 4) carbon atoms, for example an ethenyl (vinyl), propenyl (allyl), iso-propenyl, butenyl, ethinyl, propinyl, butinyl, acetylenyl, propargyl, isoprenyl or hex-2-enyl group. Preferably, alkenyl groups have one or two (especially preferably one) double bond(s), and alkynyl groups have one or two (especially preferably one) triple bond(s).

Furthermore, the terms alkyl, alkenyl and alkynyl refer to groups in which one or more hydrogen atoms have been replaced by a halogen atom (preferably F or Cl) such as, for example, a 2,2,2-trichloroethyl or a trifluoromethyl group.

The expression heteroalkyl refers to an alkyl, alkenyl or alkynyl group in which one or more (preferably 1 to 8; especially preferably 1, 2, 3 or 4) carbon atoms have been replaced by an oxygen, nitrogen, phosphorus, boron, selenium, silicon or sulfur atom (preferably by an oxygen, sulfur or nitrogen atom) or by a SO or a $SO_2$ group. The expression heteroalkyl furthermore refers to a carboxylic acid or to a group derived from a carboxylic acid, such as, for example, acyl, acylalkyl, alkoxycarbonyl, acyloxy, acyloxyalkyl, carboxyalkylamide or alkoxycarbonyloxy.

Preferably, a heteroalkyl group contains from 1 to 12 carbon atoms and from 1 to 8 heteroatoms selected from oxygen, nitrogen and sulfur (especially oxygen and nitrogen). Especially preferably, a heteroalkyl group contains from 1 to 6 (e.g. 1, 2, 3 or 4) carbon atoms and 1, 2, 3 or 4 (especially 1, 2 or 3) heteroatoms selected from oxygen, nitrogen and sulfur (especially oxygen and nitrogen). The term $C_1$-$C_6$ heteroalkyl refers to a heteroalkyl group containing from 1 to 6 carbon atoms and 1, 2, 3 or 4 heteroatoms selected from O, S and/or N (especially O and/or N). The term $C_1$-$C_4$ heteroalkyl refers to a heteroalkyl group containing from 1 to 4 carbon atoms and 1, 2 or 3 heteroatoms selected from O, S and/or N (especially O and/or N). Furthermore, the term heteroalkyl refers to groups in which one or more hydrogen atoms have been replaced by a halogen atom (preferably F or Cl).

Further preferably, the expression heteroalkyl refers to an alkyl group as defined above (straight-chain or branched) in which one or more (preferably 1 to 6; especially preferably 1, 2, 3 or 4) carbon atoms have been replaced by an oxygen, sulfur or nitrogen atom or a CO group; this group preferably contains from 1 to 6 (e.g. 1, 2, 3 or 4) carbon atoms and 1, 2, 3 or 4 (especially 1, 2 or 3) heteroatoms selected from oxygen, nitrogen and sulfur (especially oxygen and nitrogen); this group may preferably be substituted by one or more (preferably 1 to 6; especially preferably 1, 2, 3 or 4) fluorine, chlorine, bromine or iodine atoms or OH, =O, SH, =S, $NH_2$, =NH, $N_3$, CN or $NO_2$ groups.

Examples of heteroalkyl groups are groups of formulae: $R^a$—O—$Y^a$—, $R^a$—S—$Y^a$—, $R^a$—SO—$Y^a$—, $R^a$—$SO_2$—$Y^a$—, $R^a$—N($R^b$)—$SO_2$—$Y^a$—, $R^a$—$SO_2$—N($R^b$)—$Y^a$—, $R^a$—N($R^b$)—$Y^a$—, $R^a$—CO—$Y^a$—, $R^a$—C(=N$R^d$)—$Y^a$—, $R^a$—O—CO—$Y^a$—, $R^a$—CO—O—$Y^a$—, $R^a$—CO—N($R^b$)—$Y^a$—, $R^a$—N($R^b$)—CO—$Y^a$—, $R^a$—N($R^b$)—C(=N$R^d$)—$Y^a$—, $R^a$—O—CO—N($R^b$)—$Y^a$—, $R^a$—N($R^b$)—CO—O—$Y^a$—, $R^a$—N($R^b$)—CO—N($R^c$)—$Y^a$—, $R^a$—O—CO—O—$Y^a$—, $R^a$—N($R^b$)—C(=N$R^d$)—N($R^c$)—$Y^a$—, $R^a$—CS—$Y^a$—, $R^a$—O—CS—$Y^a$—, $R^a$—CS—O—$Y^a$—, $R^a$—CS—N($R^b$)—$Y^a$—, $R^a$—N($R^b$)—CS—$Y^a$—, $R^a$—O—CS—N($R^b$)—$Y^a$—, $R^a$—N($R^b$)—CS—O—$Y^a$—, $R^a$—N($R^b$)—CS—N($R^c$)—$Y^a$—, $R^a$—O—CS—O—$Y^a$—, $R^a$—S—CO—$Y^a$—, $R^a$—CO—S—$Y^a$—, $R^a$—S—CO—N($R^b$)—$Y^a$—, $R^a$—N($R^b$)—CO—S—$Y^a$—, $R^a$—S—CO—O—$Y^a$—, $R^a$—O—CO—S—$Y^a$—, $R^a$—S—CO—S—$Y^a$—, $R^a$—S—CS—$Y^a$—, $R^a$—CS—S—$Y^a$—, $R^a$—S—CS—N($R^b$)—$Y^a$—, $R^a$—N($R^b$)—CS—S—$Y^a$—, $R^a$—S—CS—O—$Y^a$—, $R^a$—O—CS—S—$Y^a$—, wherein $R^a$ being a hydrogen atom, a $C_1$-$C_6$ alkyl, a $C_2$-$C_6$ alkenyl or a $C_2$-$C_6$ alkynyl group; $R^b$ being a hydrogen atom, a $C_1$-$C_6$ alkyl, a $C_2$-$C_6$ alkenyl or a $C_2$-$C_6$ alkynyl group; $R^c$ being a hydrogen atom, a $C_1$-$C_6$ alkyl, a $C_2$-$C_6$ alkenyl or a $C_2$-$C_6$ alkynyl group; $R^d$ being a hydrogen atom, a $C_1$-$C_6$ alkyl, a $C_2$-$C_6$ alkenyl or a $C_2$-$C_6$ alkynyl group and $Y^a$ being a bond, a $C_1$-$C_6$ alkylene, a $C_2$-$C_6$ alkenylene or a $C_2$-$C_6$ alkynylene group, wherein each heteroalkyl group contains at least one carbon atom and one or more hydrogen atoms may be replaced by fluorine or chlorine atoms.

Specific examples of heteroalkyl groups are methoxy, trifluoromethoxy, ethoxy, n-propyloxy, isopropyloxy, butoxy, tert-butyloxy, methoxymethyl, ethoxymethyl, —$CH_2CH_2OH$, —$CH_2OH$, —$SO_2Me$, —NHAc, methoxyethyl, 1-methoxyethyl, 1-ethoxyethyl, 2-methoxyethyl or 2-ethoxyethyl, methylamino, ethylamino, propylamino, isopropylamino, dimethylamino, diethylamino, isopropylethylamino, methylamino methyl, ethylamino methyl, diisopropylamino ethyl, methylthio, ethylthio, isopropylthio, enol ether, dimethylamino methyl, dimethylamino ethyl, acetyl, propionyl, butyryloxy, acetyloxy, methoxycarbonyl, ethoxycarbonyl, propionyloxy, acetylamino or propionylamino, carboxymethyl, carboxyethyl or carboxypropyl, N-ethyl-N-methylcarbamoyl or N-methylcarbamoyl. Further examples of heteroalkyl groups are nitrile (—ON), isonitrile, cyanate, thiocyanate, isocyanate, isothiocyanate and alkylnitrile groups.

The expression cycloalkyl refers to a saturated or partially unsaturated (for example, a cycloalkenyl group) cyclic group that contains one or more rings (preferably 1 or 2), and contains from 3 to 14 ring carbon atoms, preferably from 3 to 10 (especially 3, 4, 5, 6 or 7) ring carbon atoms. The expression cycloalkyl refers furthermore to groups in which one or more hydrogen atoms have been replaced by fluorine, chlorine, bromine or iodine atoms or by OH, =O, SH, =S, $NH_2$, =NH, $N_3$ or $NO_2$ groups, thus, for example, cyclic ketones such as, for example, cyclohexanone, 2-cyclohexenone or cyclopentanone. Further specific examples of cycloalkyl groups are a cyclopropyl, cyclobutyl, cyclopentyl, spiro[4,5]decanyl, norbornyl, cyclohexyl, cyclopentenyl, cyclohexadienyl, decalinyl, bicyclo[4.3.0]nonyl, tetraline, cyclopentylcyclohexyl, fluorocyclohexyl or cyclohex-2-enyl group.

The expression heterocycloalkyl refers to a cycloalkyl group as defined above in which one or more (preferably 1, 2 or 3) ring carbon atoms have been replaced by an oxygen, nitrogen, silicon, selenium, phosphorus or sulfur atom (preferably by an oxygen, sulfur or nitrogen atom) or a SO group or a $SO_2$ group. A heterocycloalkyl group has preferably 1 or 2 ring(s) containing from 3 to 10 (especially 3, 4, 5, 6 or 7) ring atoms (preferably selected from C, O, N and S). The expression heterocycloalkyl refers furthermore to groups that are substituted by fluorine, chlorine, bromine or iodine atoms or by OH, =O, SH, =S, $NH_2$, =NH, $N_3$ or $NO_2$ groups. Examples are a piperidyl, prolinyl, imidazolidinyl, piperazinyl, morpholinyl (e.g. —$N(CH_2CH_2)_2O$), urotropinyl, pyrrolidinyl, tetrahydrothiophenyl, tetrahydropyranyl, tetrahydrofuryl or 2-pyrazolinyl group and also lactames, lactones, cyclic imides and cyclic anhydrides.

The expression alkylcycloalkyl refers to groups that contain both cycloalkyl and also alkyl, alkenyl or alkynyl groups in accordance with the above definitions, for example alkylcycloalkyl, cycloalkylalkyl, alkylcycloalkenyl, alkenylcycloalkyl and alkynylcycloalkyl groups. An alkylcycloalkyl group preferably contains a cycloalkyl group that contains one or two rings having from 3 to 10 (especially 3, 4, 5, 6 or 7) ring carbon atoms, and one or two alkyl, alkenyl or alkynyl groups (especially alkyl groups) having 1 or 2 to 6 carbon atoms.

The expression heteroalkylcycloalkyl refers to alkylcycloalkyl groups as defined above in which one or more (preferably 1, 2 or 3) carbon atoms have been replaced by an oxygen, nitrogen, silicon, selenium, phosphorus or sulfur atom (preferably by an oxygen, sulfur or nitrogen atom) or a SO group or a $SO_2$ group. A heteroalkylcycloalkyl group preferably contains 1 or 2 rings having from 3 to 10 (especially 3, 4, 5, 6 or 7) ring atoms, and one or two alkyl, alkenyl, alkynyl or heteroalkyl groups (especially alkyl or heteroalkyl groups) having from 1 or 2 to 6 carbon atoms. Examples of such groups are alkylheterocycloalkyl, alkylheterocycloalkenyl, alkenylheterocycloalkyl, alkynylheterocycloalkyl, heteroalkylcycloalkyl, heteroalkylheterocycloalkyl and heteroalkylheterocycloalkenyl, the cyclic groups being saturated or mono-, di- or tri-unsaturated.

The expression aryl refers to an aromatic group that contains one or more rings containing from 6 to 14 ring carbon atoms, preferably from 6 to 10 (especially 6) ring carbon atoms. The expression aryl refers furthermore to groups that are substituted by fluorine, chlorine, bromine or iodine atoms or by OH, SH, $NH_2$, $N_3$ or $NO_2$ groups. Examples are the phenyl, naphthyl, biphenyl, 2-fluorophenyl, anilinyl, 3-nitrophenyl or 4-hydroxyphenyl group.

The expression heteroaryl refers to an aromatic group that contains one or more rings containing from 5 to 14 ring atoms, preferably from 5 to 10 (especially 5 or 6 or 9 or 10) ring atoms, comprising one or more (preferably 1, 2, 3 or 4) oxygen, nitrogen, phosphorus or sulfur ring atoms (preferably O, S or N). The expression heteroaryl refers furthermore to groups that are substituted by fluorine, chlorine, bromine or iodine atoms or by OH, SH, $N_3$, $NH_2$ or $NO_2$ groups. Examples are pyridyl (e.g. 4-pyridyl), imidazolyl (e.g. 2-imidazolyl), phenylpyrrolyl (e.g. 3-phenylpyrrolyl), thiazolyl, isothiazolyl, 1,2,3-triazolyl, 1,2,4-triazolyl, oxadiazolyl, thiadiazolyl, indolyl, indazolyl, tetrazolyl, pyrazinyl, pyrimidinyl, pyridazinyl, 4-hydroxypyridyl (4-pyridonyl), 3,4-hydroxypyridyl (3,4-pyridonyl), oxazolyl, isoxazolyl, triazolyl, tetrazolyl, isoxazolyl, indazolyl, indolyl, benzimidazolyl, benzoxazolyl, benzisoxazolyl, benzthiazolyl, pyridazinyl, quinolinyl, isoquinolinyl, pyrrolyl, purinyl, carbazolyl, acridinyl, pyrimidyl, 2,3'-bifuryl, pyrazolyl (e.g. 3-pyrazolyl) and isoquinolinyl groups.

The expression aralkyl refers to groups containing both aryl and also alkyl, alkenyl, alkynyl and/or cycloalkyl groups in accordance with the above definitions, such as, for example, arylalkyl, arylalkenyl, arylalkynyl, arylcycloalkyl, arylcycloalkenyl, alkylaryl-cycloalkyl and alkylarylcycloalkenyl groups. Specific examples of aralkyls are toluene, xylene, mesitylene, styrene, benzyl chloride, o-fluorotoluene, 1H-indene, tetraline, dihydronaphthalene, indanone, phenylcyclopentyl, cumene, cyclohexylphenyl, fluorene and indane. An aralkyl group preferably contains one or two aromatic ring systems (especially 1 or 2 rings), each containing from 6 to 10 carbon atoms and one or two alkyl, alkenyl and/or alkynyl groups containing from 1 or 2 to 6 carbon atoms and/or a cycloalkyl group containing 5 or 6 ring carbon atoms.

The expression heteroaralkyl refers to groups containing both aryl and/or heteroaryl groups and also alkyl, alkenyl, alkynyl and/or heteroalkyl and/or cycloalkyl and/or heterocycloalkyl groups in accordance with the above definitions. A heteroaralkyl group preferably contains one or two aromatic ring systems (especially 1 or 2 rings), each containing from 5 or 6 to 9 or 10 ring atoms (preferably selected from C, N, O and S) and one or two alkyl, alkenyl and/or alkynyl groups containing 1 or 2 to 6 carbon atoms and/or one or two heteroalkyl groups containing 1 to 6 carbon atoms and 1, 2 or 3 heteroatoms selected from O, S and N and/or one or two cycloalkyl groups each containing 5 or 6 ring carbon atoms and/or one or two heterocycloalkyl groups, each containing 5 or 6 ring atoms comprising 1, 2, 3 or 4 oxygen, sulfur or nitrogen atoms.

Examples are aryiheteroalkyl, arylheterocycloalkyl, arylheterocycloalkenyl, arylalkylheterocycloalkyl, arylalkenylheterocycloalkyl, arylalkynylheterocycloalkyl, arylalkylheterocycloalkenyl, heteroarylalkyl, heteroarylalkenyl, heteroarylalkynyl, heteroarylheteroalkyl, heteroarylcycloalkyl, heteroarylcycloalkenyl, heteroaryl-heterocycloalkyl, heteroarylheterocycloalkenyl, heteroarylalkylcycloalkyl, heteroaryl-alkylheterocycloalkenyl, heteroarylheteroalkylcycloalkyl, heteroarylheteroalkyl-cycloalkenyl and heteroarylheteroalkylheterocycloalkyl groups, the cyclic groups being saturated or mono-, di- or tri-unsaturated. Specific examples are a tetrahydroisoquinolinyl, benzoyl, phthalidyl, 2- or 3-ethylindolyl, 4-methylpyridino, 2-, 3- or 4-methoxyphenyl, 4-ethoxyphenyl, 2-, 3- or 4-carboxyphenylalkyl group.

As already stated above, the expressions cycloalkyl, heterocycloalkyl, alkylcycloalkyl, heteroalkylcycloalkyl, aryl, heteroaryl, aralkyl and heteroaralkyl also refer to groups that are substituted by fluorine, chlorine, bromine or iodine atoms or by OH, =O, SH, =S, $NH_2$, =NH, $N_3$ or $NO_2$ groups.

The term halogen refers to F, Cl, Br or I.

When an aryl, heteroaryl, cycloalkyl, alkylcycloalkyl, heteroalkylcycloalkyl, heterocycloalkyl, aralkyl or heteroaralkyl group contains more than one ring, these rings may be bonded to each other via a single or double bond or these rings may be annulated.

Owing to their substitution, the compounds of the present invention may contain one or more centers of chirality. The present invention therefore includes both all pure enantiomers and all pure diastereomers and also mixtures thereof in any mixing ratio. The present invention moreover also includes all cis/trans-isomers of the compounds of the present invention and also mixtures thereof. The present invention moreover includes all tautomeric forms of the compounds of the present invention.

The present invention further provides pharmaceutical compositions comprising one or more compounds described herein or a pharmaceutically acceptable salt, solvate or hydrate thereof, optionally in combination with one or more carrier substances and/or one or more adjuvants. Optionally, the pharmaceutical compositions of the present invention may further comprise a β-lactam antibiotic.

The present invention furthermore provides compounds or pharmaceutical compositions as described herein for use as a medicament, especially for use in the treatment of bacterial infections, especially caused by various Gram-negative bacteria such as Enterobacterales (e.g. *E. coli, K. pneumoniae*), *Acinetobacter baumannii* and *P. aeruginosa.*

The present invention further provides a compound as described herein or a pharmaceutical composition as defined herein for the preparation of a medicament, especially for use in the treatment of bacterial infections.

Examples of pharmacologically acceptable salts of sufficiently basic compounds are salts of physiologically acceptable mineral acids like hydrochloric, hydrobromic, sulfuric and phosphoric acid; or salts of organic acids like methanesulfonic, p-toluenesulfonic, lactic, acetic, trifluoroacetic, citric, succinic, fumaric, maleic and salicylic acid. Further, a sufficiently acidic compound may form alkali or earth alkali metal salts, for example sodium, potassium, lithium, calcium or magnesium salts; ammonium salts; or organic base salts, for example methylamine, dimethylamine, trimethylamine, triethylamine, ethylenediamine, ethanolamine, choline hydroxide, meglumin, piperidine, morpholine, tris-(2-hydroxyethyl)amine, lysine or arginine salts; all of which are also further examples of salts of the compounds described herein.

The compounds described herein may be solvated, especially hydrated. The hydratization/hydration may occur during the process of production or as a consequence of the hygroscopic nature of the initially water-free compounds. The solvates and/or hydrates may e.g. be present in solid or liquid form.

The therapeutic use of the compounds described herein, their pharmacologically acceptable salts, solvates and hydrates, respectively, as well as formulations and pharmaceutical compositions also lie within the scope of the present invention.

In general, the compounds and pharmaceutical compositions described herein will be administered by using the known and acceptable modes known in the art.

For oral administration such therapeutically useful agents can be administered by one of the following routes: oral, e.g. as tablets, dragees, coated tablets, pills, semisolids, soft or hard capsules, for example soft and hard gelatine capsules, aqueous or oily solutions, emulsions, suspensions or syrups, parenteral including intravenous, intramuscular and subcutaneous injection, e.g. as an injectable solution or suspension, rectal as suppositories, by inhalation or insufflation, e.g. as a powder formulation, as microcrystals or as a spray (e.g. liquid aerosol), transdermal, for example via an transdermal delivery system (TDS) such as a plaster containing the active ingredient or intranasal. For the production of such tablets, pills, semisolids, coated tablets, dragees and hard, e.g. gelatine, capsules the therapeutically useful product may be mixed with pharmaceutically inert, inorganic or organic excipients as are e.g. lactose, sucrose, glucose, gelatine, malt, silica gel, starch or derivatives thereof, talc, stearinic acid or their salts, dried skim milk, and the like. For the production of soft capsules one may use excipients as are e.g. vegetable, petroleum, animal or synthetic oils, wax, fat, and polyols. For the production of liquid solutions, emulsions or suspensions or syrups one may use as excipients e.g. water, alcohols, aqueous saline, aqueous dextrose, polyols, glycerin, lipids, phospholipids, cyclodextrins, vegetable, petroleum, animal or synthetic oils. Especially preferred are lipids and more preferred are phospholipids (preferred of natural origin; especially preferred with a particle size between 300 to 350 nm) preferred in phosphate buffered saline (pH=7 to 8, preferred 7.4). For suppositories one may use excipients as are e.g. vegetable, petroleum, animal or synthetic oils, wax, fat and polyols. For aerosol formulations one may use compressed gases suitable for this purpose, as are e.g. oxygen, nitrogen and carbon dioxide. The pharmaceutically useful agents may also contain additives for conservation, stabilization, e.g. UV stabilizers, emulsifiers, sweetener, aromatizers, salts to change the osmotic pressure, buffers, coating additives and antioxidants.

In general, in the case of oral or parenteral administration to adult humans weighing approximately 80 kg, a daily dosage of about 1 mg to about 10,000 mg, preferably from about 5 mg to about 1,000 mg, should be appropriate, although the upper limit may be exceeded when indicated. The daily dosage can be administered as a single dose or in divided doses, or for parenteral administration, it may be given as continuous infusion or subcutaneous injection.

Compounds of Formula (I) inhibit metallo-β-lactamases and can synergize the antibacterial effects of β-lactam antibiotics against microorganisms normally resistant to β-lactam antibiotics as a result of the presence of the metallo-β-lactamases. Compounds of the present invention are effective against metallo-β-lactamases and their combination with a β-lactam antibiotic can provide effective treatment of bacterial infections caused by metallo-β-lactamase-producing microorganisms.

Examples for β-lactam antibiotics include cephalosporines such as cefepime and ceftazidime; and carbapenems such as imipenem and meropenem.

According to a preferred embodiment, the compounds of the present invention are administered in combination or together with imipenem and meropenem.

According to a moreover preferred embodiment, the present invention provides a method for inhibiting β-lactamase in a subject which comprises administering to the subject an effective amount of a compound of formula (I), or a pharmaceutically acceptable salt thereof, optionally in combination with a β-lactam antibiotic.

According to a further preferred embodiment, the present invention provides a method for inhibiting β-lactamase in a subject which comprises administering to the subject a pharmaceutical composition comprising a compound of formula (I), or a pharmaceutically acceptable salt thereof, and a β-lactam antibiotic.

According to a moreover preferred embodiment, the present invention provides a method for treating a bacterial infection which comprises administering to a subject in need of such treatment a therapeutically effective amount of a compound of formula (I), or a pharmaceutically acceptable salt thereof, in combination with a β-lactam antibiotic.

According to a further preferred embodiment, the present invention provides a method for treating a bacterial infection which comprises administering to a subject in need of such treatment a pharmaceutical composition comprising a compound of formula (I), or a pharmaceutically acceptable salt thereof, and a β-lactam antibiotic.

EXAMPLES

General. All reagents were used from commercial suppliers without further purification. Procedures were not optimized regarding yield. NMR spectra were recorded on a Bruker AV 500 (500 MHz) spectrometer. Chemical shifts are given in parts per million (ppm) and referenced against the residual proton, $^{1}H$, or carbon, $^{13}C$, resonances of the >99% deuterated solvents as internal reference. Coupling constants (J) are given in Hertz. Data are reported as follows: chemical shift, multiplicity (s=singlet, d=doublet, t=triplet, m=multiplet, dd=doublet of doublets, br=broad and combinations of these), coupling constants, and integration. Liquid chromatography-mass spectrometry was performed on a LC-MS system, consisting of a Dionex UltiMate 3000 pump, autosampler, column compartment and detector (Thermo Fisher Scientific, Dreieich, Germany) and ESI quadrupole MS (MSQ Plus or ISQ EC, Thermo Fisher Scientific, Dreieich, Germany). High-resolution mass was determined by LC-MS/MS using Thermo Scientific Q Exactive Focus Orbitrap LC-MS/MS system. Purity of compounds synthesized by us was determined by LC-MS using the area percentage method on the UV trace recorded at a wavelength of 254 nm and found to be >95%. For purification of compounds further referred to as "purified by flash chromatorgaphy", the crude product was adsorbed on silica (Macherey-Nagel, 60 M, 0.04-0.063 mm) and was purified using a CombiFlash Rf 150 (Teledyne Isco) System equipped with RediSepRf silica columns. For normal phase flash chromatography, a Redisnap Rf 4 g or 12 g silica column was used with a solvent system of either hexane/EtOAc (gradient 0% to 100%) or DCM/MeOH (gradient 0 to 5%). For reversed phase chromatography, a Redisnap Rf C18 4 g column was used with a solvent system of H2O+0.1% FA/MeCN+0.1% FA (gradient 0% to 100%).

Synthesis of N-aryl Mercaptopropionamides

The overall synthetic route for N-aryl mercaptopropionamide derivatives is outlined in Scheme 1. Following route A (a), neat reaction of the corresponding anilines with commercially available 3-mercaptopropionic acid at 120° C. afforded the corresponding compounds. For synthesis of further compounds, route B (b) was followed. For the activation of 3-(acetylthio) mercaptopropionic acid, three different coupling reagents were used. A coupling reaction using HATU in presence of diisopropylethylamine furnished compounds JMK-313 and JMK-320, while activation of 3-(acetylthio) mercaptopropionic acid with ethylchloroformate in presence of trimethylamine gave compounds JMK-292 and JMK-307. Activation with EDC·HCl, followed by reaction with the corresponding aniline afforded the other compounds. Hydrolysis of thioacetate using sodium hydroxide in methanol at room temperature provided the final corn pounds.

Scheme 1 Reaction scheme for synthesis of N-aryl mercaptopropionamides.

a)

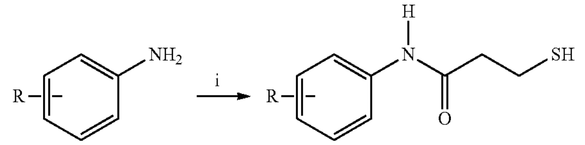

HIPS1685: R = 2-CO$_2$Me (19%) iii
HIPS1686: R = 2-CO$_2$H (>99%)
HIPS1687: R = 3-OH (40%)
HIPS5585: R = 3-NHSO$_2$Me (19%)
HIPS5190: R = 4-OH (53%)
HIPS5188: R = 4-Ac (15%)
HIPS1447: R = 3,4-di Cl (51%)

b)

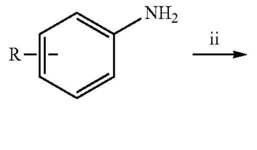

-continued

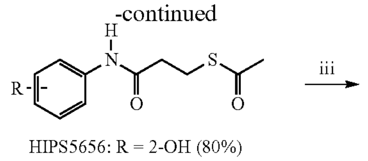

HIPS5656: R = 2-OH (80%)
HIPS5591: R = 2-NHSO$_2$Me (30%)
HIPS5670: R = 3-CO$_2$H (25%)
JMK-307: R = 3-SO$_3$H (50%)
JMK-299: R = 3-NO$_2$ (65%)
JMK-306: R = 3-CH$_2$NEt$_2$ (88%)
HIPS5658: R = 3-CH$_2$NHBoc (63%) iv
CKA-146: R = 3-CH$_2$NH$_2$ (>99%)
HIPS5590: R = 4-CO$_2$Me (29%)
HIPS5663: R = 4-CO$_2$H (79%)
JMK-308: R = 4-NHBoc (88%) iv
JMK-311: R = 4-NH$_2$ (>99%)
HIPS5671: R = 4-CH$_2$— 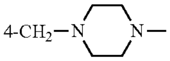 — (61%)
HIPS5642: R = 4-SO$_2$NMe$_2$ (38%)
JMK-313: R = 4-SO$_2$NHCONH$_2$ (56%)
JMK-320: R = 4-SO$_2$NHCNHNH$_2$ (57%)
JMK-292: R = 4-SO$_2$— 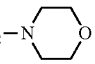 (55%)

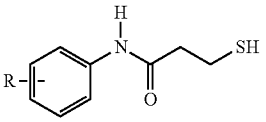

HIPS5661: R = 2-OH (>99%)
HIPS5654: R = 2-NHSO$_2$Me (33%)
HIPS5694: R = 3-CO$_2$H (67%)
HIPS5672: R = 3-SO$_3$H (51%)
HIPS5662: R = 3-NO$_2$ (70%)
HIPS5664: R = 3-CH$_2$NEt$_2$ (23%)
HIPS5640: R = 3-CH$_2$NH$_2$ (45%)
HIPS5586: R = 4-CO$_2$Me (45%)
HIPS5695: R = 4-CO$_2$H (95%)
HIPS5666: R = 4-NH$_2$ (40%)
HIPS5696: R = 4-CH$_2$— 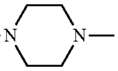 — (56%)
HIPS5665: R = 4-SO$_2$NMe$_2$ (91%)
HIPS5682: R = 4-SO$_2$NHCONH$_2$ (65%)
HIPS5683: R = 4-SO$_2$NHCNHNH$_2$ (32%)
HIPS5659: R = 4-SO$_2$— 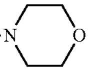 (63%)

a) (Route A)
i. 3-mercaptopropionic acid, neat, overnight, 120° C.
iii. 2 M NaOH, MeOH, 2-3 h, r.t. or 2 M NaOH, 1,4-dioxane, 2-3 h, r.t b) (Route B)
ii. 3-(acetylthio) mercaptopropionic acid, EDC·HCl, DCM, overnight, r.t.; or 3-(acetylthio) mercaptopropionic acid, ClCO$_2$Et, Et$_3$N, THF, overnight, 0° C. to r.t.; or 3-(acetylthio) mercaptopropionic acid, HATU, DIEA, DCM, overnight, r.t.
iii. 2 M NaOH, MeOH, 2-3 h, r.t.
iv. TFA, DCM, overnight, r.t.

General Procedure A-1: Synthesis of Thioacetate Derivatives Using EDC·HCl as Coupling Reagent (Scheme 1, Reaction ii)

3-(Acetylthio) propionic acid (1.2-1.5 eq) was placed in a vial and dissolved in DCM. To this solution, EDC-HCl (1.2-1.5 eq) was added and left to form a cloudy solution.

Then, the corresponding amine (1.0 eq) was added, and the reaction was stirred at room temperature (r.t.). The reaction was monitored using TLC or LC-MS. The reaction was quenched with 1 M HCl until pH=1. The organic phase was washed with saturated aqueous NaCl solution (1×) and then dried over anh. $Na_2SO_4$. The product was filtered and concentrated. Purification was done by column chromatography.

General Procedure A-2: Synthesis of Thioacetate Derivatives Using Ethylchloroformate as Coupling Reagent (Scheme 1, Reaction ii)

3-(Acetylthio) propionic acid (1.2 eq) was dissolved in THF and cooled in an ice-bath. $Et_3N$ (1.2 eq) was added, followed by addition of $ClCO_2Et$ (1.3 eq). After 5 minutes, the ice-bath was removed and the reaction was stirred at r.t. for 30 minutes. The corresponding amine (1.0 eq) was slowly added. The reaction was monitored using TLC or LC-MS. After the reaction was completed, volatiles were evaporated under reduced pressure and the crude product was purified using column chromatography or preparative HPLC ($H_2O$+0.05% FA/ACN+0.05% FA 95/5→5/95).

General Procedure A-3: Synthesis of Thioacetate Derivatives Using HATU as Coupling Reagent (Scheme 1, Reaction ii)

3-(Acetylthio) propionic acid (1.5 eq), HATU (1.5 eq) and DIEA (1.5 eq) were dissolved in DCM. The corresponding amine (1.0 eq) was added and the reaction was stirred at r.t. for 2 days. Volatiles were evaporated under reduced pressure and the crude product was purified using preparative HPLC ($H_2O$+0.05% FA/ACN+0.05% FA 95/5→5/95).

General Procedure B: Hydrolysis of Thioacetate (Scheme 1, Reaction iii)

Thioacetate (1.0 eq) was dissolved in methanol or compound HIPS1685 (1.0 eq) was dissolved in 1,4-dioxane under Ar atmosphere and 2 M aq. solution of NaOH (2.0-3.0 eq) or solid NaOH (3.0-4.0 eq) was added. The reaction was stirred 1-2 h at r.t. After quenching with 1 M HCl, the product was extracted 3 times with EtOAc. The combined organic extracts were washed with saturated aqueous NaCl solution, dried over anh. $Na_2SO_4$ and filtered. The solvent was removed under reduced pressure. Purification was done via flash chromatography. In case of more polar compounds, instead of quenching the reaction with 1 M HCl, pH was adjusted to acidic using Amberlite IR-120. After filtration, Amberlite was washed with MeOH (3×), solvent was evaporated and the product was purified using preparative HPLC ($H_2O$+0.05% FA/ACN+0.05% FA 95/5→5/95).

General Procedure C: Synthesis of Free Thiols (Scheme 1, Reaction i)

Aniline (1.0 eq) was placed in a crimp vial. The vial was evacuated and flushed with Ar followed by addition of 3-mercaptopropionic acid (1.2-1.5 eq). The vial was flushed with Ar again and heated to 120° C. for 5 h. The crude product was purified using reverse phase flash chromatography ($H_2O$+0.1% FA/ACN+0.1% FA 95/5→5/95).

General Procedure D: Deprotection of the Tert-Butyloxycarbonyl Group (Scheme 1, Reaction iv)

To a solution of the corresponding Boc-protected compound (1.0 eq) in DCM, a concentrated solution of TFA (5.0-7.0 eq) was added and the reaction was stirred overnight at r.t. Volatiles were evaporated and the crude product was used in the next step without further purification.

N-(3,4-Dichlorophenyl)-3-mercaptopropanamide (HIPS1447)

Compound HIPS1447 was synthesized according to general procedure C, using 3,4-dichloroaniline (150 mg, 1.25 mmol) and 3-mercaptopropionic acid (330 μL, 3.75 mmol). The product was purified by reverse flash chromatography (5% ACN to 100% ACN). Final product was obtained as white solid (120 mg, 51%). $^1H$ NMR (500 MHz, DMSO-d6) δ ppm: 10.27 (s, 1H), 8.00 (d, J=2.4 Hz, 1H), 7.56 (d, J=8.8 Hz, 1H), 7.47 (dd, J=8.8, 2.4 Hz, 1H), 2.77-2.71 (m, 2H), 2.66-2.62 (m, 2H), 2.45-2.40 (m, 1H). $^{13}C$ NMR (126 MHz, DMSO) δ 169.91, 139.14, 130.96, 130.68, 124.53, 120.24, 119.08, 40.33, 19.47. HRMS ($ESI^-$ m/z calcd. for $C_9H_8Cl_2NOS$ $[M-H]^-$ 247.97091 found 247.97091.

Synthesis of 3-(3-(acetylthio)propanamido)benzoic acid (HIPS5670)

Compound HIPS5670 was synthesized according to general procedure A-1, using 3-aminobenzoic acid (130 mg, 0.95 mmol), 3-(acetylthio) propionic acid (210 mg, 1.42 mmol) and EDC HCl (272 mg, 1.42 mmol) in DCM (10 mL). The product was purified using preparative HPLC. The final product was obtained as white powder (62 mg, 25%) $^1H$ NMR (500 MHz, DMSO-$d_6$) δ ppm: 12.96 (br s, 1H), 8.21 (s, 1H), 7.79 (d, J=6.6 Hz, 1H), 7.61 (d, J=7.9 Hz, 1H), 7.41 (t, J=7.9 Hz, 1H), 3.09 (t, J=6.8 Hz, 2H), 2.65 (t, J=6.8 Hz, 2H), 2.33 (s, 3H). $^{13}C$ NMR (126 MHz, DMSO-$d_6$) δ ppm: 195.50, 169.45, 167.23, 139.23, 131.49, 129.06, 124.06, 123.08, 119.80, 35.30, 30.61, 24.25. HRMS ($ESI^+$) m/z calcd. for $C_{12}H_{14}NO_4S$ $[M+H]^+$ 268.06380, found 268.06381.

Synthesis of 3-(3-mercaptopropanamido)benzoic acid (HIPS5694)

Compound HIPS5694 was synthesized according to general procedure B, using compound HIPS5670 (62 mg, 0.23 mmol) and NaOH (37 mg, 0.92 mmol) in MeOH (2 mL). The product was purified using preparative HPLC. Final product was obtained as white powder (35 mg, 67%). $^1H$ NMR (500 MHz, DMSO-$d_6$) δ ppm: 10.15 (s, 1H), 8.23 (t, J=2.0 Hz, 1H), 7.84-7.78 (m, 1H), 7.60 (m, 1H), 7.41 (t, J=7.9 Hz, 1H), 2.75 (m, 2H), 2.63 (t, J=6.7 Hz, 2H), 2.40 (t, J=7.8 Hz, 1H). $^{13}C$ NMR (126 MHz, DMSO-$d_6$) δ ppm: 169.61, 167.22, 139.26, 128.93, 123.96, 123.06, 119.85, 40.29, 19.63. HRMS ($ESI^-$) m/z calcd. for $C_{10}H_{10}NO_3S$ $[M-H]^-$ 224.03868, found 224.03814.

Further Compounds Shown in Scheme 1:

The other compounds shown in Scheme 1 have been prepared and characterized according to the procedures described above.

Biological Assays

Protein expression and purification. The expression of IMP-7, VIM-1, and NDM-1 was performed according to the protocol previously published by Klingler et al. (Klingler, F. M.; Wichelhaus, T. A.; Frank, D.; Cuesta-Bernal, J.; El-Delik, J.; Müller, H. F.; Sjuts, H.; Göttig, S.; Koenigs, A.; Pos, K. M.; et al. Approved Drugs Containing Thiols as Inhibitors of Metallo-β-Lactamases: Strategy to Combat Multidrug-Resistant Bacteria. *J. Med. Chem.* 2015, 58 (8), 3626-3630. https://doi.org/10.1021/jm501844d) with slight modifications.

In vitro inhibition assay. Activity assays for NDM-1, VIM-1, VIM-2 and IMP-7 were carried out, as described by Klingler et al. Final protein concentrations were 0.5 nM (NDM-1), 4.0 nM (VIM-1), and 0.1 nM (IMP-7) in a 50 mM HEPES buffer (pH 7.5, 0.01% Triton X-100) Substrate (Fluorocillin™ (Invitrogen, Darmstadt, Germany) was dissolved in assay buffer to a final concentration of 888 nM. Test compounds were dissolved and pre-diluted in DMSO (final concentration: 1%). In a black polystyrol 96-well plate (Corning) an amount of 1 μL of the respective inhibitor solution at different concentrations was incubated with 89 μL of respective protein containing buffer for 30 minutes at room temperature. 10 μL of substrate solution was added. The readout of the emitted fluorescence was started immediately (45 s for 30 cycles) using a Tecan Infinite F200Pro (Tecan Group Ltd; excitation at 495 nm and emission at 525 nm). Blank controls were performed without enzyme. Positive controls were performed with enzyme but without inhibitor. The inhibitory activity of each test compound was measured in three independent experiments. For calculation of $IC_{50}$ values, data obtained from measurements with eight different inhibitor concentrations were used. For the evaluation of the sigmoidal dose response equation (variable slope with four parameters) GraphPad Prism 5 (GraphPad Software, La Jolla, CA, USA) was used.

Cytotoxicity assays and Selectivity assays. Cytotoxicity assays on HepG2, HEK293 and A549 cells and selectivity assays on various MMPs were performed as described previously (Haupenthal, J.; Baehr, C.; Zeuzem, S.; Piiper, A. RNAse A-like Enzymes in Serum Inhibit the Anti-Neoplastic Activity of SiRNA Targeting Polo-like Kinase 1. *Int. J. Cancer* 2007, 121 (1), 206-210. https://doi.org/10.1002/ijc.22665).

MIC assays. Minimal inhibitory concentrations (MICs) of imipenem and the compounds of the present invention against MBL-positive and MBL-negative clinical isolates and/or against transformed *E. coli* strains producing different recombinant metallo-β-lactamases were determined according to the microdilution method established by Clinical and Laboratory Standards Institute (CLSI) (Wayne, P. A. Clinical and Laboratory Standards Institute Methods for Dilution Antimicrobial Susceptibility Tests for Bacteria That Grow Aerobically Standard, Approval CDM-A.; *Clin. Lab. Stand. Inst.* 2018, 91).

Fractional inhibitory concentration index (FICI). The checkerboard assay was performed to test for synergy in vitro. The microtiter-plates were set up with serial doubling dilutions of the test compounds (16-1024 mg/L) and imipenem (1-1024 mg/L). FICIs≤0.5 were defined as synergistic; FICIs from >0.5 to ≤1 were defined as additive; FICIs from 1 to ≤4 were defined as indifferent and FICIs>4 were defined as antagonistic (Doern, C. D. When Does 2 plus 2 Equal 5? A Review of Antimicrobial Synergy Testing. *J. Clin. Microbial.* 2014, 52 (12), 4124-4128. https://doi.org/10.1128/JCM.01121-14).

Zebrafish Toxicity. Toxicity testing was performed according to the procedure described in the literature (Maes, J.; Verlooy, L.; Buenafe, O. E.; de Witte, P. A. M.; Esguerra, C. V.; Crawford, A. D. Evaluation of 14 Organic Solvents and Carriers for Screening Applications in Zebrafish Embryos and Larvae. *PLoS One* 2012, 7 (10), 1-9. https://doi.org/10.1371/journal.pone.0043850) with minor modifications using zebrafish embryos of the AB wild-type line at 1 day post-fertilization. Embryos were collected and kept in a Petri dish at 28° C. until the next day in 0.3× Danieau's medium (17 mM NaCl, 2 mM KCl, 1.8 mM $Ca(NO_3)_2$, 1.5 mM HEPES (pH 7.1-7.3), 0.12 mM $MgSO_4$, and 1.2 μM methylene blue). The toxicity assay was performed using a 96-well plate with one embryo per well and 10 embryos per condition. To obtain compound concentrations between 30 μM and 150 μM, solutions of the compounds were prepared freshly using 0.3× Danieau's medium with a final DMSO concentration of 1% (v/v). Single zebrafish embryos were placed in wells and directly incubated in the corresponding compound solutions. Monitoring of developmental defects, heart rate, touch-evoked locomotion response, and survival rate was done daily (up to 120 hpf) via microscopy (Table x). All of the described experiments were performed with zebrafish embryos <120 h post-fertilization (hpf) and are not classified as animal experiments according to EU Directive 2010/63/EU. Protocols for husbandry and care of adult animals are in accordance with the German Animal Welfare Act (§ 11 Abs. One TierSchG).

Table 1 shows the in vitro activity of the compounds of the present invention against three MBLs (IMP-7, VIM-1 and NDM-1) belonging to class B1 in a kinetic fluorescence-based activity assay.

TABLE 1

Structures and MBL inhibitory activity of N-aryl mercaptopropionamides.[a]

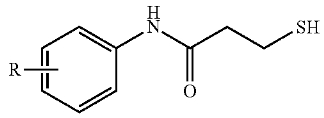

| Compound | R | $IC_{50}$ (μM) NDM-1 | IMP-7 | VIM-1 |
|---|---|---|---|---|
| HIPS1686 | 2-$CO_2H$ | 3.4 ± 0.1 | 4.1 ± 0.3 | 2.2 ± 0.2 |
| HIPS5654 | 2-$NHSO_2Me$ | 7.0 ± 0.3 | n.i. | 1.9 ± 0.2 |
| HIPS5661 | 2-OH | 2.2 ± 0.4 | 3.3 ± 0.4 | 0.2 ± 0.0 |
| HIPS1685 | 2-$CO_2Me$ | 1.3 ± 0.2 | 1.0 ± 0.1 | n.i. |
| HIPS5640 | 3-$CH_2NH_2$ | 6.5 ± 0.4 | 5.5 ± 0.7 | 0.8 ± 0.1 |
| HIPS1687 | 3-OH | 2.7 ± 0.5 | 1.4 ± 0.2 | 0.1 ± 0.0 |
| HIPS5662 | 3-$NO_2$ | 2.5 ± 0.2 | 2.6 ± 0.1 | 0.1 ± 0.0 |
| HIPS5664 | 3-$CH_2NEt_2$ | 6.5 ± 0.4 | 5.5 ± 0.7 | 0.8 ± 0.1 |
| HIPS5672 | 3-$SO_3H$ | 1.3 ± 0.0 | 3.6 ± 0.3 | 1.6 ± 0.1 |
| HIPS5585 | 3-$NHSO_2Me$ | 2.2 ± 0.3 | 1.3 ± 0.0 | 1.3 ± 0.0 |
| HIPS5694 | 3-$CO_2H$ | 4.0 ± 0.0 | 6.4 ± 0.6 | 1.2 ± 0.0 |
| HIPS1447 | 3,4-di-Cl | 1.3 ± 0.0 | 5.0 ± 0.6 | 0.1 ± 0.0 |
| HIPS5586 | 4-$CO_2Me$ | 2.8 ± 0.1 | 1.1 ± 0.7 | 0.1 ± 0.0 |
| HIPS5188 | 4-COMe | 1.5 ± 0.3 | 5.5 ± 0.1 | 0.4 ± 0.1 |
| HIPS5190 | 4-OH | 4.0 ± 1.1 | 3.4 ± 0.7 | 0.2 ± 0.0 |
| HIPS5695 | 4-$CO_2H$ | 1.0 ± 0.4 | n.i. | 0.6 ± 0.0 |
| HIPS5665 | 4-$SO_2NMe_2$ | 2.8 ± 0.1 | 2.1 ± 0.2 | 0.8 ± 0.0 |
| HIPS5666 | 4-$NH_2$ | 6.5 ± 0.5 | 2.1 ± 0.3 | 0.5 ± 0.0 |
| HIPS5682 | 4-$SO_2NHCONH_2$ | 8.6 ± 0.2 | 12.6 ± 2.8 | 2.0 ± 0.1 |
| HIPS5683 | 4-$SO_2NHCNHNH_2$ | 2.1 ± 0.1 | 3.3 ± 0.4 | 0.5 ± 0.0 |
| HIPS5659 | 4-$SO_2$— 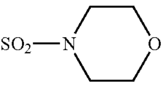 | 2.5 ± 0.2 | 7.1 ± 1.4 | 1.7 ± 0.3 |
| HIPS5696 | 4-$CH_2$— 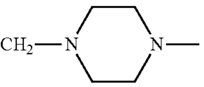 | 6.4 ± 0.6 | 5.8 ± 0.4 | 1.5 ± 0.1 |

[a]Means and SD of at least two independent experiments.

In addition to its potency, HIPS1447 is selective over six representative human matrix metalloproteases (MMPs) (Table 2a), and shows no significant toxicity when tested on three different human cell lines (Table 2b).

TABLE 2a

Activity of HIPS1447 against human MMPs, n.i = <10% inhibition.

| | | |
|---|---|---|
| % Inh. @ 100 μM of HIPS1447 | MMP-1 | n.i. |
| | MMP-2 | 15.8 ± 13.5 |
| | MMP-3 | n.i. |
| | MMP-7 | n.i. |
| | MMP-8 | 38.2 ± 24.8 |
| | MMP-14 | 17.9 ± 7.8 |

TABLE 2b

| Cytotoxicity of HIPS1447 against human cell lines. | | |
|---|---|---|
| $IC_{50}$ [μM] | HepG2 | >100 |
| | HEK293 | >100 |
| | A549 | >100 |

Also other compounds of the present invention showed no cytotoxic effects at a concentration of 100 μM.

Antibacterial activities and minimum inhibitory concentrations (ICs). The minimum inhibitory concentration (MIC) for several compounds (HIPS1447, HIPS1686, HIPS5682, HIPS5683, HIPS5694, HIPS5695, HIPS540, HIPS5672) in different isolates from *E. coli* and *P. aeruginosa* has been evaluated. All compounds showed no intrinsic antibacterial activity.

Since the utility of carbapenems is threatened by MBLs, imipenem has been chosen as β-lactam antibiotic for combination. Imipenem is a broad-spectrum member of the carbapenem family of β-lactam antibiotics. A series of compounds has been selected to be tested in a synergistic checkerboard assay.

Compound HIPS1447 was tested in imipenem-resistant *P. aeruginosa* producing VIM-2 at a single concentration (1024 μg/mL), yielding a 64-fold decreased MIC value.

Table 3 shows that HIPS1686, bearing no intrinsic antibacterial activity, is able to maintain the effect of imipenem.

TABLE 3

MIC (μg/mL) of imipenem for *E. coli* producing NDM-1 in the presence of HIPS 1686.

| Substance | MIC in mg/L |
|---|---|
| Imipenem (IMI) | 128 |
| HIPS1686 | >1024 |
| IMI + HIPS1686 (constant 1024 μg/ml) | 1 |
| IMI + HIPS1686 (constant 256 μg/ml) | 1 |
| IMI + HIPS1686 (constant 64 μg/ml) | 4 |

TABLE 4

Synergistic antimicrobial activity (checkerboard assay) of imipenem with HIPS1686 against *E. coli* NDM-1 (T2359)

| HIPS1686 | Imipenem MIC * in mg/L |
|---|---|
| — | 128 |
| +256 mg/L | 2 |
| +128 mg/L | 2 |
| +64 mg/L | 8 |
| +32 mg/L | 16 |
| +16 mg/L | 64 |
| +8 mg/L | 64 |
| +4 mg/L | 64 |

* The median of three experiments is given.

TABLE 5

Synergistic antimicrobial activity of imipenem with HIPS1686 against clinical isolates expressing various MBLs.

| | MIC (mg/L) | | | | | | |
|---|---|---|---|---|---|---|---|
| Substance | *K. pneumoniae* NDM-1 (T2301) | *E. cloacae* NDM-1 (T2311) | *S. marcescens* NDM-1 (T2352) | *E. coli* NDM-5 (T2351) | *E. cloacae* VIM-1 (T2353) | *P. aeruginosa* IMP-1 (T2325) | *E. cloacae* GIM-1 (T2218) |
| Imipenem | 16 | 16 | 256 | 16 | 32 | 64 | 2 |
| Imipenem (+HIPS1686 256 mg/L) | 1 | 1 | 4 | 2 | 4 | 32 | 0.5 |

TABLE 6

Synergistic antimicrobial activity of imipenem with several compounds against *E. coli* NDM-1 (T2359)

| | Imipenem MIC in mg/L | | | | | |
|---|---|---|---|---|---|---|
| HIPSHIPS | HIPS5640 | HIPS5672 | HIPS5682 | HIPS5683 | HIPS5694 | HIPS5695 |
| — | 128 | 128 | 128 | 128 | 128 | 128 |
| +128 mg/L | 64 | 2 | 16 | 16 | ≤0.5 | 8 |
| +64 mg/L | 128 | 32 | 64 | 64 | 2 | 32 |
| +32 mg/L | 128 | 128 | 128 | 128 | 8 | 128 |
| +16 mg/L | 128 | 128 | 128 | 128 | 64 | 128 |
| +8 mg/L | 128 | 128 | 128 | 128 | 64 | 128 |
| +4 mg/L | 128 | 128 | 128 | 128 | 128 | 128 |
| +2 mg/L | 128 | 128 | 128 | 128 | 128 | 128 |

TABLE 7

Synergistic antimicrobial activity of imipenem with several compounds against *E. coli* VIM-1 (T2544)

| | Imipenem MIC in mg/L | | | | | |
|---|---|---|---|---|---|---|
| HIPS | HIPS5640 | HIPS5672 | HIPS5682 | HIPS5683 | HIPS5694 | HIPS5695 |
| — | 32 | 64 | 32 | 32 | 32 | 32 |
| +128 mg/L | 16 | 4 | 2 | 2 | 0.5 | 1 |
| +64 mg/L | 32 | 8 | 8 | 8 | 8 | 2 |
| +32 mg/L | 32 | 32 | 16 | 16 | 16 | 4 |
| +16 mg/L | 32 | 32 | 32 | 32 | 16 | 16 |
| +8 mg/L | 32 | 64 | 32 | 32 | 32 | 16 |
| +4 mg/L | 32 | 64 | 32 | 32 | 32 | 16 |
| +2 mg/L | 32 | 64 | 32 | 32 | 32 | 16 |

TABLE 8

Synergistic antimicrobial activity of imipenem with several compounds against *E. coli* IMP-1 (T2360)

| | Imipenem MIC in mg/L | | | | |
|---|---|---|---|---|---|
| HIPS | HIPS5672 | HIPS5682 | HIPS5683 | HIPS5694 | HIPS5695 |
| — | 2 | 2 | 2 | 2 | 2 |
| +128 mg/L | 0.5 | 1 | 0.5 | 0.5 | 0.5 |
| +64 mg/L | 1 | 1 | 1 | 0.5 | 0.5 |
| +32 mg/L | 1 | 1 | 1 | 1 | 1 |
| +16 mg/L | 1 | 1 | 1 | 1 | 1 |
| +8 mg/L | 2 | 2 | 1 | 1 | 2 |
| +4 mg/L | 2 | 2 | 1 | 2 | 2 |
| +2 mg/L | 2 | 2 | 2 | 2 | 2 |

TABLE 9

Intrinsic antimicrobial activity of HIPS5694

| Bacteria | HIPS 5694 MIG (mg/L) |
|---|---|
| *E. coli* NDM-7 (T2239) | >256 |
| *K. pneumoniae* NDM-1 (T2301) | >256 |
| *E. cloacae* NDM-1 (T2311) | >256 |
| *S. marcescens* NDM-1 (T2352) | >256 |
| *E. coli* NDM-5 (T2351) | >256 |
| *E. cloacae* VIM-1 (T2353) | >256 |
| *P. aeruginosa* VIM-1 (T2357) | >256 |
| *P. aeruginosa* IMP-1 (T2325) | >256 |
| *E. cloacae* GIM-1 (T2218) | >256 |
| *A. baumannii* OXA-23 (T2434) | >256 |
| *E. coli* KPC-2 (T2435) | >256 |

TABLE 10

Synergistic antimicrobial activity of imipenem with HIPS5694 against clinical isolates expressing various MBLs and non-MBL carbapenemases.

| | MIC (mg/L) | |
|---|---|---|
| Bacteria | Imipenem | Imipenem (+HIPS 5694 128 mg/L) |
| *E. coli* NDM-7 (T2239) | 32 | 2 |
| *K. pneumoniae* NDM-1 (T2301) | 16 | 0.5 |
| *E. cloacae* NDM-1 (T2311) | 8 | 1 |
| *S. marcescens* NDM-1 (T2352) | 256 | 4 |
| *E. coli* NDM-5 (T2351) | 8 | 2 |
| *E. cloacae* VIM-1 (T2353) | 4 | 2 |

In Vivo Toxicity in Zebrafish Model.

Owing to its in vitro activities against three MBLs, selectivity against human MMPs and the lack of cytotoxicity against three human cell lines, compounds HIPS1686, HIPS5682 and HIPS5683 were subjected to a toxicity study based on zebrafish larvae. This non-mammalian in vivo model has a high genetic homology to humans and provides follow-up information on the type of toxicity encountered (Chakraborty, C. et al, (2016). *J. Nanobiotechnology,* 14, 1-13.). In addition, it can also evaluate lethality and malformation during development of embryonic zebrafish (MacRae, C. A., Peterson, R. T. (2015). *Nat. Rev. Drug Discov.* 14, 721-731). The tested compounds showed a maximum tolerated concentration (MTC) of ≥150 μM.

The invention claimed is:

1. A compound of formula (I):

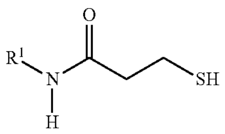

(I)

wherein $R^1$ is a substituted phenyl group or a substituted heteroaryl group containing 5 or 6 ring atoms selected from C, O, N and S, wherein the substituents are independently selected from groups of formula $-O-C_{1-6}$ alkyl, $-NHC_{1-6}$ alkyl, $-N(C_{1-6}\ alkyl)_2$, $-COOH$, $-COOMe$, $-COMe$, $-NHSO_2Me$, $-SO_2NMe_2$, $-SO_2NCNH_2NH_2$, $-CH_2N(CH_2CH_3)_2$, $-SO_2NHCONH_2$, $-SO_2NHC(NH)NH_2$, $-CH_2N(CH_2CH_2)_2NCH_3$, $-SO_3H$, $-SO_2NH_2$, $-CONH_2$, $-CH_2NH_2$, $-CN$, $-S-C_{1-6}$ alkyl, NHAc, $-SO_2-N(CH_2CH_2)_2O$, $-NHCONH_2$, $-SO_2Me$ and cyclopropyl, or a pharmaceutically acceptable salt thereof.

2. A compound according to claim 1, wherein $R^1$ is an optionally substituted phenyl group.

3. A compound according to claim 1, wherein group $R^1$ is substituted by one, two or three substituents.

4. A compound according to claim 1, wherein group $R^1$ is substituted by one or two substituents.

5. A compound selected from the following compounds, or a salt thereof:

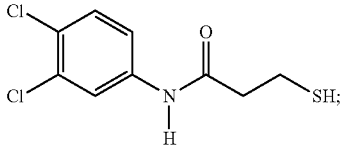

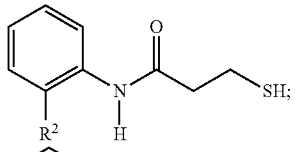

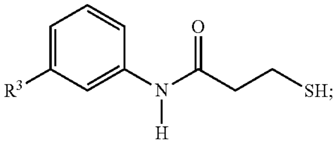

and

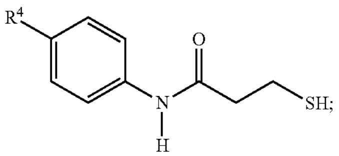

wherein $R^2$ is —COOH, —$NHSO_2Me$, —OH or —COOMe; $R^3$ is —OH, —COOH, —$NHSO_2Me$, —$CH_2NH_2$, —$NO_2$, —$SO_3H$ or —$CH_2N(CH_2CH_3)_2$; and $R^4$ is —OH, —$NH_2$, —COOH, —COOMe, —COMe, —$SO_2NMe_2$, —$SO_2$—$N(CH_2CH_2)_2O$, —$SO_2NHCONH_2$, —$SO_2NHC(NH)NH_2$ or —$CH_2N(CH_2CH_2)_2NCH_3$.

6. A pharmaceutical composition comprising a compound according to claim 1 and optionally one or more carrier substances and/or one or more adjuvants.

7. The pharmaceutical composition according to claim 6, further comprising a β-lactam antibiotic.

8. A method for treating a bacterial infection which comprises administering to a subject in need of such treatment a therapeutically effective amount of a compound according to claim 1, or a pharmaceutically acceptable salt thereof, in combination with a β-lactam antibiotic.

9. A method for treating a bacterial infection which comprises administering to a subject in need of such treatment a pharmaceutical composition according to claim 6, and a β-lactam antibiotic.

10. A method for treating a bacterial infection which comprises administering to a subject in need of such treatment a pharmaceutical composition according to claim 7.

11. A method for treating a bacterial infection which comprises administering to a subject in need of such treatment a therapeutically effective amount of a compound of formula (I), or a pharmaceutically acceptable salt thereof, in combination with a β-lactam antibiotic:

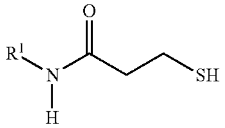

(I)

wherein $R^1$ is an optionally substituted phenyl group or an optionally substituted heteroaryl group containing 5 or 6 ring atoms selected from C, O, N and S, wherein the optional substituents are independently selected from fluorine, chlorine, bromine and iodine and groups of formula —OH, —O—$C_{1-6}$ alkyl, —$NH_2$, —$NHC_{1-6}$ alkyl, —$N(C_{1-6}$ alkyl$)_2$, —COOH, —COOMe, —COMe, —$NHSO_2Me$, —$SO_2NMe_2$, —$SO_2NCNH_2NH_2$, —$CH_2N(CH_2CH_3)_2$, —$SO_2NHCONH_2$, —$SO_2NHC(NH)NH_2$, —$CH_2N(CH_2CH_2)_2NCH_3$, —$SO_3H$, —$SO_2NH_2$, —$CONH_2$, —$CH_2NH_2$, —CN, —$C_{1-6}$ alkyl, —SH, —S—$C_{1-6}$ alkyl, NHAc, —$SO_2$—$N(CH_2CH_2)_2O$, —$NO_2$, —C≡CH, —$NHCONH_2$, —$SO_2Me$ and cyclopropyl.

12. The method according to claim 11, wherein $R^1$ is an optionally substituted phenyl group.

13. The method according to claim 11, wherein group $R^1$ is substituted by one, two or three substituents.

14. The method according to claim 11, wherein group $R^1$ is substituted by one or two substituents.

15. The method according to claim 11, wherein the optional substituents are independently selected from Cl, —OH, —$NH_2$, —COOH, —COOMe, —COMe, —$NHSO_2Me$, —$SO_2NMe_2$, —$CH_2NH_2$, —$NO_2$, —$SO_2$—$N(CH_2CH_2)_2O$, —$SO_3H$, —$CH_2N(CH_2CH_3)_2$, —$SO_2NHCONH_2$, —$SO_2NHC(NH)NH_2$, —$CH_2N(CH_2CH_2)_2NCH_3$ and —$SO_2NCNH_2NH_2$.

16. A pharmaceutical composition comprising a compound according to claim 5 and optionally one or more carrier substances and/or one or more adjuvants.

17. The pharmaceutical composition according to claim 16, further comprising a β-lactam antibiotic.

18. A method for treating a bacterial infection which comprises administering to a subject in need of such treatment a therapeutically effective amount of a compound according to claim 5, or a pharmaceutically acceptable salt thereof, in combination with β-lactam antibiotic.

19. A method for treating a bacterial infection which comprises administering to a subject in need of such treatment a pharmaceutical composition according to claim 16, and a β-lactam antibiotic.

20. A method for treating a bacterial infection which comprises administering to a subject in need of such treatment a pharmaceutical composition according to claim 17.

* * * * *